United States Patent [19]

Hall et al.

[11] Patent Number: 5,336,648
[45] Date of Patent: Aug. 9, 1994

US005336648A

[54] ZEOLITE CATALYSTS SUITABLE FOR HYDROCARBON CONVERSION

[75] Inventors: Anthony H. P. Hall, Surrey; Alistair W. Winstanley, Middlesex, both of England

[73] Assignee: The British Petroleum Company p.l.c., London, Great Britain

[21] Appl. No.: 56,217

[22] Filed: Apr. 30, 1993

Related U.S. Application Data

[62] Division of Ser. No. 728,914, Jul. 12, 1991, Pat. No. 5,235,122.

[30] Foreign Application Priority Data

Jul. 12, 1990 [GB] United Kingdom ............... 9015355

[51] Int. Cl.$^5$ .................... B01J 29/06; B01J 29/28
[52] U.S. Cl. .................................. 502/61; 502/77
[58] Field of Search .............................. 502/61, 77

[56] References Cited

U.S. PATENT DOCUMENTS

| | | | |
|---|---|---|---|
| 3,013,985 | 12/1961 | Breck et al. | 502/61 |
| 3,431,219 | 3/1969 | Argauer et al. | 502/61 |
| 4,946,813 | 8/1990 | Shum | 502/61 |

FOREIGN PATENT DOCUMENTS 0048863  11/1985  World Int. Prop. O. ............ 502/61

*Primary Examiner*—Carl F. Dees
*Attorney, Agent, or Firm*—Kay, Sharpe, Beall, Fagan, Minnich & McKee

[57] ABSTRACT

A novel catalyst composition comprising a crystalline aluminosilicate having a molar ratio of silica to alumina of at least 5:1, the aluminosilicate carrying gallium and copper, is useful in the conversion at elevated temperature of a $C_2$–$C_{12}$ hydrocarbon feedstock into aromatic hydrocarbons.

6 Claims, No Drawings

ZEOLITE CATALYSTS SUITABLE FOR HYDROCARBON CONVERSION

This is a division of co-pending application Ser. No. 07/728,914 filed Jul. 12, 1991, now U.S. Pat. No. 5,235,122.

The present invention relates to zeolite catalysts suitable for hydrocarbon conversion.

UK Patent Specification No. 1561590 discloses a process for the production of aromatic hydrocarbons, comprising contacting at elevated temperature a $C_3$–$C_{12}$ hydrocarbon feedstock with a defined zeolite catalyst containing gallium. EP-A-50021 discloses a similar process using a $C_2$ hydrocarbon feedstock.

Surprisingly, it has now been found that the yield of aromatics in a process of this type can be improved by incorporating copper into the catalyst.

Accordingly, the present invention provides a catalyst composition comprising a crystalline aluminosilicate having a molar ratio of silica to alumina of at least 5:1, said aluminosilicate carrying gallium and copper.

The invention further provides a process for producing aromatic hydrocarbons, which comprises bringing a catalyst composition according to the invention into contact with a $C_2$–$C_{12}$ hydrocarbon feedstock at elevated temperature.

By $C_2$–$C_{12}$ feedstock is meant throughout this specification a feedstock containing a single hydrocarbon component or mixtures of saturated and/or unsaturated $C_2$–$C_{12}$ hydrocarbons. The feedstock is preferably a $C_3$–$C_4$ hydrocarbon feedstock. $C_3$ and $C_4$ feeds containing propane, propene, isobutane and/or isobutene in the feedstock are particularly useful. Other useful feedstocks include naphtha, in which case the process is a reforming process.

The optimum temperature for the process according to the invention depends on the feedstock used. Preferably, the temperature is in the range of from 300° to 700° C. When using a $C_3$–$C_4$ hydrocarbon feedstock, the temperature is preferably in the range of from 450° to 600° C. Preferably, the feedstock is passed over the catalyst composition in the vapour phase, if desired in admixture with an inert gas, for example nitrogen. Reaction pressures are suitably from 100 to 2000 KPa absolute, preferably 200 to 1000 KPa absolute.

A wide range of crystalline aluminosilicates are useful as the basis of the catalyst composition according to the invention. The silica to alumina ratio is preferably in the range of from 10:1 to 200:1, especially 10:1 to 70:1. Typical zeolites include ZSM-5, ZSM-8, ZSM-11, ZSM-12 and ZSM-35, which are described in U.S. Pat. No. 3970544. A further suitable aluminosilicate is that designated zeolite Theta-1 as described in EP-A-57049. The use of zeolites ZSM-11 and, especially, ZSM-5, is preferred.

In the catalyst composition according to the invention, the gallium may have been introduced by ion exchange. In this case, gallium ions may be provided as an aqueous solution of a gallium salt, for example gallium nitrate, gallium chloride or gallium sulphate. Such catalysts may be produced by conventional ion exchange techniques and the catalysts so produced are subsequently dried. For example an aqueous solution of a gallium compound such as gallium nitrate may be placed in contact with the aluminosilicate at ambient or elevated temperature, for example by refluxing. The exchanged aluminosilicate may then be separated for example by decantation followed by filtration, washed several times with deionised water and finally dried. Before addition to the aqueous solution of the gallium compound, the aluminosilicate may be acid treated.

Alternatively, the gallium may be deposited on the aluminosilicate; it may be impregnated on the surface of the aluminosilicate or incorporated in the intracrystalline zeolite cavities as a gallium compound which gives rise to gallium oxide during activation of the catalyst prior to contact with the hydrocarbon feedstock. An example of a suitable gallium compound is gallium nitrate. Conventional impregnation techniques may be used to produce these catalysts. The impregnation for example may be achieved by preparing excess of a solution, for example an aqueous solution of a gallium compound, e.g. gallium nitrate, and adding the aluminosilicate to this aqueous solution with thorough stirring to form a paste. The paste may subsequently be dried for example using an elevated temperature in vacuum. The so-called incipient wetness technique is also a useful impregnation technique. Here, a solution of a gallium salt is added to an amount of the aluminosilicate sufficient to absorb the entire volume of liquid.

Where the catalyst composition is prepared by using a compound of gallium which ionises in aqueous solution, for example gallium nitrate, it is inevitable that some of the gallium ions will be exchanged with the cations in the aluminosilicate even if the preparation was directed to impregnation of the aluminosilicate.

Whichever method of catalyst preparation is used, the amount of gallium present in the catalyst compositions may for instance be in the range of from 0.05 to 10%, preferably 0.1 to 7% by weight of the total aluminosilicate in the catalyst composition.

Similarly, the copper in the catalyst composition may have been introduced by ion exchange or by deposition using an aqueous or non-aqueous solution of a copper salt, in ways directly analogous to those described above for the gallium. For example, copper nitrate is a convenient salt, soluble in both water and alcohol. Impregnation may be by a variety of techniques including the so-called incipient wetness technique, rotary evaporation or refluxing. The pH value of the solution may be adjusted as appropriate. Preferably the amount of copper present in the catalyst composition is in the range of from 0.01 to 10, preferably 0.1 to 7% by weight of the total aluminosilicate in the catalyst composition.

The catalyst composition may if desired contain other metal components in addition to gallium and copper. Most preferably, the composition contains gallium and copper as the only metal components.

The aluminosilicate may suitably be used as prepared or equally suitably in a modified form, for example in the hydrogen or ammonium exchanged form.

The invention also provides a process for the preparation of a catalyst composition according to the invention, which comprises treating a crystalline aluminosilicate having a molar ratio of silica to alumina of at least 5:1, with a solution or solutions containing gallium and copper. The order of introduction of gallium and copper is immaterial. Gallium may be introduced followed by copper, copper may be introduced followed by gallium, or both may be introduced together using mixed salt solutions.

The catalyst composition according to the invention may also, if desired, contain a binder. Any suitable binder commonly used for zeolite catalysts may be used, for example silica, alumina, or a clay. The binder, if present, may be incorporated into the catalyst at any suitable stage in the catalyst preparation, either before or after the introduction of gallium and/or copper.

The catalyst composition is suitably activated prior to contact with the hydrocarbon feedstock. The activation may be carried out by heating the catalyst at a temperature of between 400° and 650° C., preferably between 500° and 600° C. Activation may, for example, be carried out in an atmosphere of nitrogen, air, or hydrogen. The activation may if desired be carried out in the reactor tube itself prior to the reaction.

The following Examples illustrate the invention.

EXAMPLE 1

250 g ZSM-5 zeolite, silica to alumina ratio 36:1, prepared by the method described in EP-A-30811, was washed with 180 ml of 70% v/v% nitric acid in 1070 ml of distilled water by stirring for 3 hours. The zeolite was filtered and washed with 4×500 ml portions of distilled water, dried under vacuum at 120° C. overnight, and then passed through a 30 mesh sieve. The sieved zeolite was calcined in a muffle furnace at 550° C. for 60 hours under a flow of air of 1700 ml/min. The furnace was then returned to room temperature.

The zeolite was refluxed for 4 hours in a 250 ml acidic gallium nitrate solution (0.025 g of Ga per ml) diluted with 1750 ml of distilled water, the pH of the resulting mixture being increased to approximately pH 2.3 with ammonia solution. The zeolite was filtered hot and washed with 4×500 ml portions of distilled water then dried in a vacuum oven at 100° C. overnight.

The dried zeolite was sieved to less than 500 microns and mixed with a silica solution (LUDOX AS40, Trade Mark) to give bound catalyst with a dry zeolite to binder ratio of 60:40. The bound zeolite was sieved to give a particle size of 8–30 mesh, and this material was treated with 16% v/v steam in air at 550° C. for 2 hours at a gas hourly space velocity of $200h^{-1}$.

EXAMPLE 2 (COMPARATIVE)

A 20 ml (14 g) portion of the product of Example 1 was placed in a stainless steel tubular reactor and the temperature was raised to 535° C. under flowing nitrogen at atmospheric pressure. When the reactor had come to temperature the reactor was purged with nitrogen for 2 hours. The pressure was raised to 200 KPa absolute and propane was passed through the reactor at a rate of 0.8 weight hourly space velocity, the furnace controls being adjusted to maintain an average bed temperature of 535° C. The reaction products were separated into gas and liquid phases in a condensor system and analysed by gas chromatography.

Conversion of propane at 47 hours on stream was found to be 58.2 wt %, with a selectivity to aromatics of 55.1 wt %.

EXAMPLE 3

A 25 ml (13.5 g) sample of the product of Example 1 was mixed with 8.7 ml of distilled water containing 0.51 g $Cu(NO_3)_2.3H_2O$ to give 1 wt % copper loading on the catalyst. The catalyst was dried at 120° C. overnight, and then tested according to the method in Example 2. The conversion of propane at 47 hours on stream was found to be 71.4 wt % with selectivity to aromatics of 57.3 wt %.

EXAMPLE 4

A 25 ml (12.80 g) sample of the product obtained in Example 1 was mixed with 12.6 ml of distilled water containing 5.825 g $Cu(NO_3)_2.3H_2O/100$ $cm^3$ of copper nitrate to give 1.5 wt % copper loading on the catalyst. The catalyst was dried overnight prior to treatment according to the method used in Example 2. The conversion of propane at 47 hours on stream was found to be 74.9 wt % with selectivity to aromatics of 55.1 wt %.

EXAMPLE 5

142 g of zeolite ZSM-5 which had been washed with nitric acid, was added with stirring, to a 1.5 liter solution of 2M ammonium nitrate, buffered to pH9 with ammonia solution. The mixture was refluxed for 3 hours, filtered and washed with distilled water (2×250 ml) and the catalyst then dried overnight at 120° C. The zeolite was passed through a 30 mesh sieve and impregnated with 69.3 ml of a pH adjusted (pH 2.3) gallium nitrate solution (0.025 g Ga/mol) such that the bound catalyst would be 0.8 wt % Ga. The Ga impregnated zeolite was bound with silica by mixing with a silica solution (LUDOX AS 40, Trade Mark) to give a zeolite to binder ratio of 60:40 when dried. The bound zeolite was sieved to give a particle size of 8–30 mesh, and this material was treated with 16% v/v steam in air at 550° C. for 2 hours at a gas hourly space velocity of $200h^{-1}$.

EXAMPLE 6 (COMPARATIVE)

20 ml (10.85 g) of the product of Example 5 was treated and tested according to the method in Example 2. The propane conversion at 46 hours on stream was found to be 53.8 wt % with a selectivity to aromatics of 54.7 wt %.

EXAMPLE 7

70 ml (41.6 g) of the product of Example 5 was mixed with 27.2 ml of distilled water containing 5.825 g $Cu(NO_3)_2.3H_2O$ per 100 mls of copper nitrate. The catalyst was dried overnight at 120° C. The catalyst was treated and tested according to the method in Example 2. The conversion of propane at 46.6 hours on stream was found to be 76.3 wt % with a selectivity to aromatics of 55.1 wt %.

We claim:

1. A catalyst composition comprising a crystalline aluminosilicate having a molar ratio of silica to alumina of at least 5:1, said aluminosilicate carrying gallium and copper.

2. A catalyst composition as claimed in claim 1, in which the crystalline aluminosilicate is ZSM-5, ZSM-8, ZSM-11, ZSM-12, ZSM-35 or Theta-1.

3. A catalyst composition as claimed in claim 1, in which the amount of gallium is in the range of from 0.05 to 10% by weight of the total aluminosilicate.

4. A catalyst composition as claimed in claim 1, in which the amount of copper is in the range of from 0.01 to 10% by weight of the total aluminosilicate in the catalyst composition.

5. A process for the preparation of a catalyst composition as claimed in claims 1, which comprises treating a crystalline aluminosilicate having a molar ratio of silica to alumina of at least 5:1, with a solution or solutions containing gallium and copper.

6. A catalyst composition comprising a crystalline aluminosilicate having a molar ratio of silica to alumina of at least 5:1, said aluminosilicate carrying gallium and copper and said composition containing gallium and copper as the only metal components.

* * * * *